United States Patent [19]
Pegg et al.

[11] Patent Number: 5,212,065
[45] Date of Patent: May 18, 1993

[54] RAPID ASSAY DEVICE

[75] Inventors: R. Kevin Pegg, Fernandina Beach; Mary S. Saunders, Monticello, both of Fla.

[73] Assignees: International Diagnostic Systems, Corp., St. Joseph, Mich.; KM Laboratories, Inc., Monticello, Fla.

[21] Appl. No.: 603,151

[22] Filed: Oct. 25, 1990

[51] Int. Cl.[5] .................................. G01N 33/543
[52] U.S. Cl. ................................ 435/7.9; 422/56; 422/57; 422/58; 422/61; 435/7.32; 435/5; 436/169; 436/527; 436/530; 436/531; 436/805; 436/808
[58] Field of Search ........................ 422/56-58, 422/61, 102, 104; 435/7.9, 5, 7.32; 436/527, 530, 531, 169, 805, 808

[56] References Cited

U.S. PATENT DOCUMENTS

| | | | |
|---|---|---|---|
| 3,791,933 | 2/1974 | Moyer et al. | 195/127 |
| 3,811,840 | 5/1974 | Bauer et al. | 23/253 TP |
| 3,888,629 | 6/1975 | Bagshawe | 23/230 B |
| 3,983,005 | 9/1976 | Goodhue et al. | 195/103.5 R |
| 4,246,339 | 1/1981 | Cole et al. | 435/7 |
| 4,278,651 | 7/1981 | Hales | 424/1 |
| 4,399,229 | 8/1983 | Kelton et al. | 436/519 |
| 4,426,451 | 1/1984 | Columbus | 422/102 |
| 4,438,067 | 3/1984 | Siddigi | 436/169 |
| 4,447,526 | 5/1984 | Rupchock et al. | 435/7 |
| 4,459,360 | 7/1984 | Marinkovich | 436/513 |
| 4,459,361 | 7/1984 | Gefter | 436/523 |
| 4,517,288 | 5/1985 | Giegel et al. | 435/7 |
| 4,632,901 | 12/1986 | Valkirs et al. | 435/5 |
| 4,665,034 | 5/1987 | Chandler | 435/287 |
| 4,704,692 | 11/1987 | Ladner | 364/496 |
| 4,748,042 | 5/1988 | Linnecke et al. | 422/56 |
| 4,948,561 | 8/1990 | Hinckley et al. | 436/808 |
| 4,962,154 | 10/1990 | Pollock et al. | 525/54.1 |
| 4,977,247 | 12/1990 | Fahnestock et al. | 435/172.3 |
| 4,994,238 | 2/1991 | Daffern et al. | 422/56 |
| 5,081,017 | 1/1992 | Longoria | 435/5 |

Primary Examiner—David Saunders
Assistant Examiner—Christopher L. Chin
Attorney, Agent, or Firm—Foley & Lardner

[57] ABSTRACT

A rapid immunoassay device comprising a single porous membrane that serves as both a reagent support and a spent reagent reservoir is disclosed. The immunoassay device directs the flow of sample and reagents within the device in a manner that eliminates both lateral diffusion and backflow of reagents without the necessity of additional external means.

28 Claims, 3 Drawing Sheets

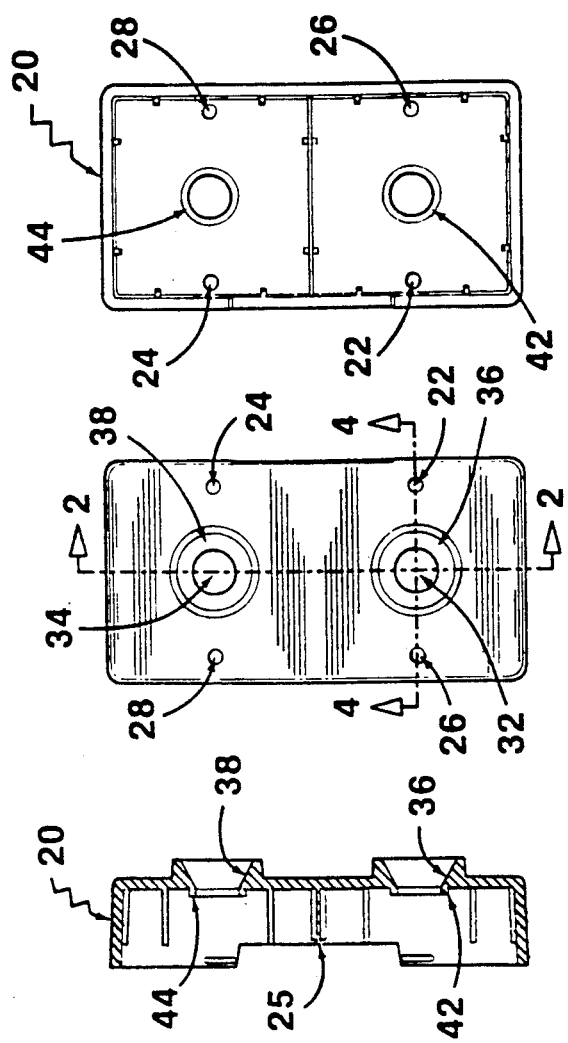

MULTIPLE BASE PLATE

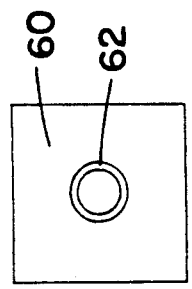
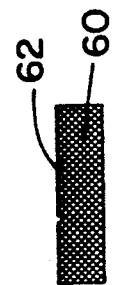
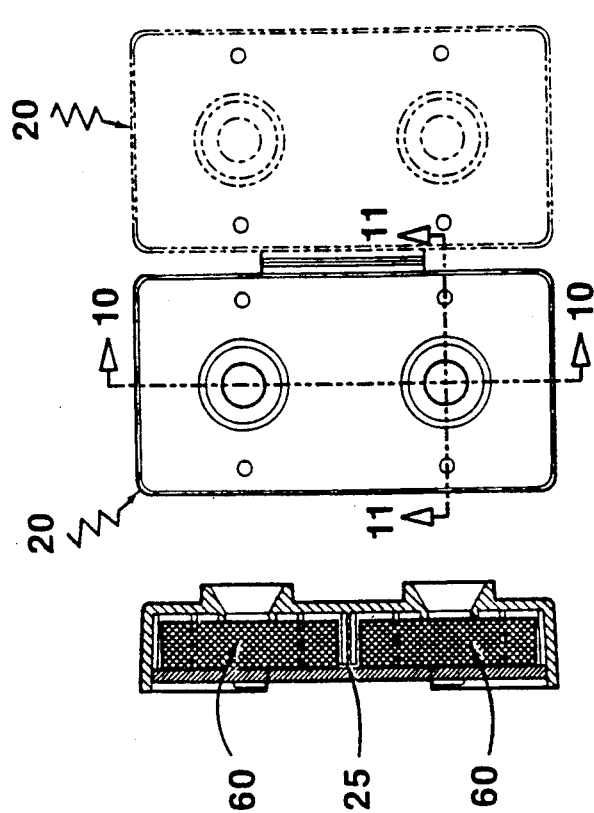
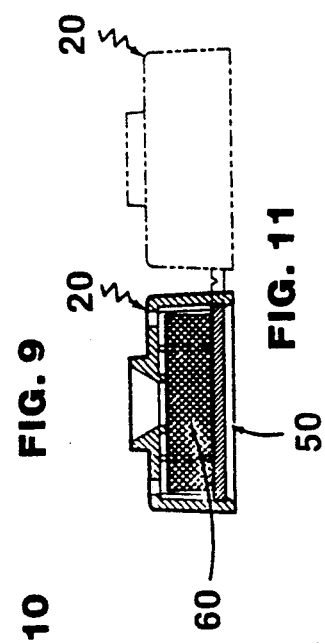

RAPID ASSAY DEVICE

BACKGROUND OF THE INVENTION

This invention relates to a device for performing immunoassays to detect a variety of antigens in a fluid sample. More particularly, this invention relates to a novel means for producing a defined reactive zone within a device and controlling reagent flow therein. It is believed that this is the first immunoassay device that employs a single porous member as both an antibody/reagent support and as a spent reagent reservoir and does not require external means to direct the flow of sample and reagents within the device.

Antibody-mediated analyses are widely utilized for the estimation of antigens in a liquid sample. Once an antibody has been developed against an antigen, the antibody can be employed as a reagent for detection of the antigen. Increasingly, samples such as serum, urine, other biological fluids and industrial fluids are analyzed using several different antibodies raised against various antigens to fully characterize the antigen make-up of the sample.

The practice of using antibodies to detect soluble antigens is well known in the art. In general, an antibody directed against an antigen of interest is immobilized on an insoluble substrate and exposed to a sample which may contain the antigen. If the sample contains the antigen, an antibody/antigen complex will form which can be detected by various means including but not limited to colorimetric, radiometric, turbidimetric and fluorometric immunoassay procedures.

The variety of apparatus and methods for controlling antibody-mediated reactions is the subject of a diverse technology. See, P. Tijssen, PRACTICE AND THEORY OF ENZYME IMMUNOASSAYS, LABORATORY TECHNIQUES IN BIOCHEMISTRY AND MOLECULAR BIOLOGY (1985). Conventional immunoassay procedures employ antibody immobilized as a coating on plastic or glass tubes. Formation of an antibody/antigen complex and the detection thereof typically require a series of incubation and rinsing steps. While effective, the method described above is substantially time consuming.

More recently a variety of strategies have been developed to form and detect antibody/antigen complexes within a single-use, disposable assay device utilizing porous antibody/reagent supports. Typical of this technology is U.S. Pat. No. 4,399,229 (Kelton et al.) in which the antibody/reagent support consists of a bacterium to which an antibody is bound, the bacterium being entrapped in a glass fiber filter. In U.S. Pat. No. 4,632,901 (Valkirs et al.), an antibody is bound to a permeable membrane which is contacted by a porous capillary member which directs the flow of sample and reagents within the device. U.S. Pat. No. 4,655,034 (Chandler) discloses a reaction chamber which employs a plurality of syringes to direct the flow of fluids within the chamber.

The foregoing devices generally require more than one member: a first member to which antibody is bound and which serves to immobilize the antibody; and at least a second member which serves as (i) a means for directing the flow of fluid within the device by capillary action or channeling and/or, (ii) as a spent fluid reservoir. In addition, these devices require a variety of means to direct sample and reagents therein such as positive pressure, vacuum and centrifugation.

Moreover, the foregoing devices allow sample and reagents to flow in both a downward and a lateral direction. Lateral reagent flow contributes to a higher incidence of inaccurate results due to the tendency of spent reagents to accumulate at the periphery of the antibody/antigen reaction zone. These reagents tend to interact and produce color reactions that are easily mistaken for a true positive or negative result.

A need therefore continues to exist for a simple immunoassay device for use in procedures to detect one or more analytes comprising a single porous material that can serve as both an antibody/reagent support and as a spent reagent reservoir. In addition, a need continues to exist for a device comprising a means for directing the flow of sample and reagents within the device in a manner that will eliminate both lateral diffusion and backflow of reagents without the necessity of additional external means.

SUMMARY OF THE INVENTION

These and other objects of the invention are achieved by providing an apparatus for use in immunoassay procedures comprising (A) a housing comprising a reservoir member and a base member, the reservoir member defining a cavity, the base member engaging the reservoir member to enclose the cavity wherein said reservoir member comprises (i) a first surface facing away from the cavity and a second surface facing into the cavity, (ii) an aperture providing an opening through both of the first and second surfaces, (iii) a first profile provided on the first surface around the aperture, (iv) at least one vent hole, (v) a second profile provided on the second surface of the aperture; (B) a porous foam member provided in the cavity, wherein a surface of the foam member is deformable by the second profile to produce a depression that surrounds an area on the surface of the foam member; and (C) a reagent-binding member provided on the surface of the foam member within the area on the surface of the foam member.

In accomplishing the foregoing object, there has been provided, in accordance with one aspect of the present invention an apparatus wherein the first profile is conical.

In accordance with another aspect of the present invention, an apparatus is provided, wherein the second profile has a circular cross section.

In accordance with a further aspect of the present invention, an apparatus is provided, wherein the porous foam member is comprised of a material selected from the group consisting of fibers of cellulose or cellulose derivatives, glass, ceramic and non-cellulose hydrocarbon materials.

In accordance with yet another aspect of the present invention, an apparatus is provided, wherein the porous foam member has a preformed depression on the surface.

In accordance with a further aspect of the present invention, an apparatus is provided, wherein the reagent-binding member includes Staphylococcal proteins A and G, and latex particles.

According to a further aspect of the present invention, an apparatus is provided, wherein the reagent-binding member includes Staphylococcal proteins A and G, and latex particles, and which further comprises antibodies which specifically bind an analyte selected from the group consisting of antibiotics, mycotoxins, coccidiostats, drugs of abuse, hormones, and bacterial antigens bound to the reagent-binding member.

According to a further aspect of the present invention, an apparatus is provided wherein the antibodies specifically bind sulfamethazine, gentamicin, aflatoxin, zearalenone, monensin, tylosin, opiates, amphetamines, methamphetamines, cocaine, barbiturates, progesterone, human chorionic gonadotropin, or *Pasteurella multocida* antigen.

According to yet another aspect of the present invention, a kit for determining an analyte in a sample is provided, comprising an apparatus, wherein the reagent-binding member includes Staphylococcal proteins A and G, and latex particles, and, in a separate container, an antibody which specifically binds the analyte and which is conjugated to an enzyme.

According to yet a further aspect of the present invention, a kit for determining an analyte in a sample is provided, wherein the antibody is conjugated to horseradish peroxidase, glucose oxidase, or alkaline phosphatase.

According to yet another aspect of the present invention, a kit for determining an analyte in a sample is provided, comprising an apparatus, wherein the reagent-binding member includes Staphylococcal proteins A and G, and latex particles, and, in a separate container, an analyte, as recited above, which is conjugated to an enzyme.

According to a further aspect of the present invention, a kit for determining an analyte in a sample is provided, wherein the analyte provided in a separate container is conjugated to horseradish peroxidase, glucose oxidase, alkaline phosphatase, or urease.

Other objects, features and advantages of the present invention will become apparent from the following detailed description. It should be understood, however, that the detailed description and the specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

FIG. 1 is a line drawing presenting a top planar view of an apparatus for performing an immunoassay in accordance with the present invention.

FIG. 2 presents a longitudinal cross-sectional view of the structure of FIG. 1.

FIG. 3 presents a bottom view of the structure of FIG. 1.

FIG. 4 presents a lateral cross-sectional view of the structure of FIG. 1.

FIG. 9 presents a top planar view of two apparatuses according to FIG. 1 engaged by a multiple base plate according to FIG. 6.

FIG. 10 presents a longitudinal cross-sectional view of the structure of FIG. 9.

FIG. 11 presents a lateral cross-sectional view of the structure of FIG. 9.

FIG. 12 presents a top planar view of a porous membrane member in accordance with the present invention.

FIG. 13 presents a lateral cross-sectional view of the structure of FIG. 12.

DETAILED DESCRIPTION OF THE PREFERRED EMBODIMENTS

Figure 5:
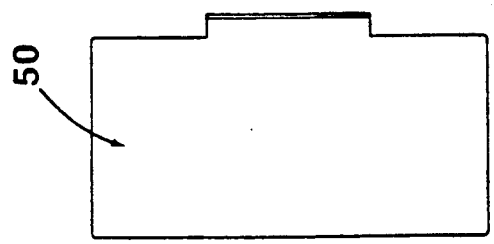
FIG. 5 presents a top planar view of a base plate in accordance with the present invention.

The immunoassay device of the present invention comprises a molded housing with a reservoir member that directs the flow of sample and reagents through an antibody/antigen reaction zone formed in a porous membrane member 60, contained by the housing. The membrane member consists of a porous material that serves as both an antibody/reagent support and as a reservoir for spent reagents and is enclosed in the housing by a retaining plate member 50.

With reference to the drawings, FIG. 1 represents a top view of a preferred embodiment of the present invention wherein a reservoir member 20 is formed with two conical or funnel-shaped profiles 36 and 38 surrounding two apertures 32 and 34 which provide openings into the two cavities formed by the reservoir member and separated by a crosswall member 25. In addition, four vent holes 22, 24, 26 and 28 are provided in the reservoir member. FIGS. 2 and 4 represent cross-sectional views of the reservoir member and show two circular profiles or rings 42 and 44 positioned directly below the conical profiles surrounding the apertures into the reservoir member. The circular rings extend into the cavities formed by the reservoir member. These circular rings are further illustrated in FIG. 3 which depicts a bottom view of the reservoir member.

Figure 6:
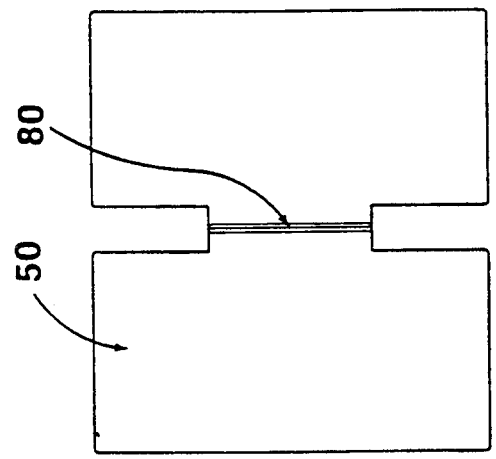
FIG. 6 presents a top planar view of a multiple base plate in accordance with the present invention.
Figure 7:
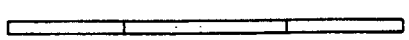
FIG. 7 presents a longitudinal cross-sectional view of the structure of FIG. 6.
Figure 8:
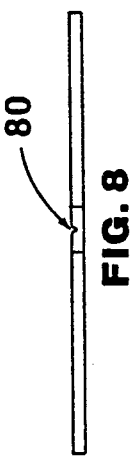
FIG. 8 presents an end view of the structure of FIG. 6.

FIG. 5 represents a base plate member 50 which, when engaged with the reservoir member as depicted in FIGS. 9-11, encloses the cavity of the reservoir member containing the porous membrane member 60. In a preferred embodiment as represented in FIG. 6, a multiple base plate which can engage two reservoir members is depicted. FIGS. 7 and 8 are cross-sectional views of the multiple base plate showing a scored area 80 which facilitates separating the multiple base plate into two individual base plates.

FIG. 9 is a top view of a preferred embodiment wherein two reservoir members are engaged by a multiple base plate thereby facilitating testing either a plurality of individual samples for one analyte or one sample for a plurality of analytes. FIGS. 10 and 11 are cross-sectional views of the preferred immunoassay device of FIG. 9. In this embodiment, a porous membrane member 60 is contained within each of the cavities formed in the reservoir member.

The base member when connected to the reservoir member applies pressure against the first surface of the porous membrane member 60 by pressing the membrane against the circular ring or profile extending downward into the cavity and thereby causing a circular depression 62 to form on the surface of the porous membrane. The resulting circular depression 62 prohibits its lateral diffusion of sample and reagents into the porous material, providing instead the desired downward flow of these fluids.

The housing may be formed of any of the plastics common to the molding arts, including but not limited to polyethylene, polypropylene, polystyrene, and polyvinyl acetate. In a preferred embodiment, the housing is formed of polystyrene. In addition, in a preferred embodiment, the base plate member is constructed in a manner that provides for connecting a plurality of reservoir members to a single base member.

The material from which the porous membrane member is comprised can be a foam of compacted fibers of cellulose or derivatives thereof or of glass, ceramic or other non-cellulose hydrocarbon materials. Suitable materials are wettable and exhibit low non-specific binding. This material is screened for optimal pore size and density in order to facilitate a controlled distribution of antibody within the membrane member and to optimize reaction kinetics.

In a preferred embodiment, the porous membrane fills the cavity of the reservoir member and is comprised of cellulose acetate. Cellulose acetate is particularly preferred because the material exhibits minimal memory. This characteristic of cellulose acetate ensures that the circular depression necessary for directing the flow of sample and reagents downward through the antibody reaction zone will be retained in the surface of the porous matrix material without continued application of pressure. In addition, the integrity of the circular depression formed on the cellulose acetateis not affected by the flow of sample and reagent fluids through the porous material or by its saturation with the foregoing fluids.

Cellulose acetate also provides for optimal wettability, low non-specific binding and can be selected for optimal pore size and density, characteristics necessary for the formation of a well-defined antibody/antigen reaction zone.

The reagent-binding member takes the form of a continuous layer or a discontinuous layer. The member is comprised of material capable of binding a wide variety of analytes including antigens and antibodies. Exemplary of such materials are natural or synthetic insoluble binding proteins, such as Staphylococcal proteins A and G, anion or cation charged polystyrene latex particles and polymeric supports, such as glucosamine polymer. Further examples of suitable reagent-binding members include polystyrene, SEPHADEX, or silica hydroxylated particles, wherein the hydroxyl groups are activated with a bridging molecule derived from, for example, cyanogen bromide, glutaraldehyde, acrolein, or phosgene; particles comprised of aminopolystyrene, polyamide, and glass or silica treated with an aminosylating agent; chitosan activated with a bridging molecule such as glutaraldehyde, phosgene and disuccimidyl suberate; carboxylated particles comprised of carboxysulfate polystyrene, nylon, and glass or silica modified with carboxy silane activated by any of the carboimide treating agents; oxirane reactive particles; and epoxy activated particles. In addition, immobilized avidin is suitable as a reagent-binding member for use with biotinylated antibodies.

In a preferred embodiment, the reagent-binding member is comprised of polystyrene latex beads. In yet a further preferred embodiment, the reagent-binding member is comprised of Protein G, derived from *Staphylococcus aureus*. In a particularly preferred embodiment, the reagent-binding member is comprised of Protein A, derived from *Staphylococcus aureus*.

The reagents which are bound by the reagent-binding member include, but are not limited to, antigens such as gentamicin, sulfamethazine and other antibiotics, opiates, cocaine, amphetamines, methamphetamine, barbiturates and other drugs of abuse, progesterone, human chorionic gonadotropin, and other hormones, aflatoxin, zearalenone, and other mycotoxins, monensin, tylosin, and other coccidiostats that are covalently bound to the reagent binding member, e.g., latex particles, by, for example, glutaraldehyde and antibodies directed against, for example, antibiotics, drugs of abuse, mycotoxins, coccidiostats and hormones. In this context the term "antibodies" is used to denote, inter alia, monoclonal or polyclonal antibodies. In addition, the term "antibodies" encompasses fragments, like Fab and F(ab')$_2$, and conjugates of such fragments and so-called "antigen binding proteins:" (single chain antibodies), in accordance, for example with U.S. Pat. No. 4,704,692, the contents of which are hereby incorporated by reference. Antibodies of this sort can be purchased from various commercial sources such as International Diagnostic Systems Corp., St. Joseph, Mich. (anti-sulfamethazine and anti-aflatoxin antibodies); Wien Laboratories, Inc., Succasunna, N.J. (anti-methamphetamine antibody); and Sigma Chemical Co., St. Louis, Mo. (anti-Pasteurella and anti-HCG antibodies).

A wide variety of enzymes can be used in practicing the present invention. Preferred enzymes are horseradish peroxidase, glucose oxidase, alkaline phosphatase, glucose-6-phosphate dehydrogenase, and $\beta$-galactosidase. Suitable substrates for the foregoing enzymes include P-nitrophenol phosphate, o-phenylenediamine, o-tolidine, 3,3',5,5'-tetramethylbenzidine, diaminobenadine, nitroblue tetrazolium, and 5-bromo,4-chloro,3-indolyl phosphate.

Without further elaboration, it is believed that one skilled in the art can, using the preceding description, utilize the present invention to its fullest extent. The following preferred specific embodiments are therefore, to be construed as merely illustrative, and not limitative of the remainder of the disclosure in any way whatsoever.

The following reagents were utilized in the examples presented below.

0.1% Bovine Serum Albumin/Phosphate Buffered Saline (BSA/PBS)

1.000 g Bovine serum albumin
8.700 g NaCl
0.230 g Na$_2$PO$_4$.H$_2$O
1.950 g K$_2$HPO$_4$.3H$_2$O
0.500 g Thimerosal
1 liter deionized water Wash Solution —Phosphate Buffered Saline with Tween (PBS-T)

8.700 g NaCl
0.230 g NaH$_2$PO$_4$.H$_2$O
1.950 g K$_2$HPO$_4$.3H$_2$O
0.010 g Thimerosal
0.125 ml Tween-20
1 liter deionized water Enzyme Diluent—0.1% Casein Trehalose Solution in Phosphate Buffered Saline 8.700 g NaCl
0.230 g NaH$_2$PO$_4$.H$_2$O
1.950 g K$_2$HPO$_4$.3H$_2$O
0.500 g Thimerosal
1.000 g Casein
0.500 g Trehalose
1 liter deionized water BCIP Solution 0.100 g 5-bromo,4-chloro,3-indolyl phosphate, disodium salt dissolved in 0.5M methanol, diluted to 1 ml in carbonate buffer.

Carbonate Buffer 0.05M Sodium Bicarbonate, pH 9.6
0.05M Sodium Carbonate

Antibody Diluent—2% Staphylococcal Protein A (SPA/PBS) Preparation Instructions

1. Prepare PBS.
   8.70 g NaCl
   0.23 g $NaH_2PO_4.H_2O$
   1.95 g $K_2HPO_4.3H_2O$
   0.01 g Thimerosal
2. Dilute 1 part SPA in 2 parts PBS.
3. Centrifuge for 20 minutes.
4. Discard clear supernatant.
5. Resuspend SPA pellet to total final volume achieved in step 2 above.
6. Vortex at slow speed until pellet is dissolved.
7. Centrifuge for 20 minutes.
8. Discard clear supernatant.
9. Resuspend SPA pellet in 0.1% PBS-Tween to a volume equal to that of the SPA alone in step 2 above.

EXAMPLE 1

Screening Porous Membrane Material for Optimal Density Characteristics Using a Competitive Inhibition Assay Samples of cellulose acetate with densities varying from 0.155 gm/cc to 0.29 gm/cc were tested to determine the optimal density of this material for use in an immunoassay designed to screen samples for 10 ppb or greater concentrations of sulfamethazine. Sulfamethazine standards containing 1, 5 and 10 ppb were prepared in 0.1% BSA/PBS buffer. Membranes prepared from samples of cellulose acetate of various densities were enclosed in the molded housing of the immunoassay device.

Five microliters of anti-sulfamethazine antibody was combined with 400 μl of 2% SPA/PBS Antibody Diluent and vortexed at slow speed for 3 seconds. After incubation at room temperature for 30 minutes with occasional vortexing, 1595 μl of PBS was added to the antibody/SPA solution and mixed by rotation. Thirty microliter aliquots of the resulting 1:400 anti-sulfamethazine antibody in 2% SPA/PBS solution were added to each of the cellulose acetate membranes. The housings containing the membranes were then covered to prevent contamination. Binding of the anti-sulfamethazine antibody to the sample membranes was accomplished by overnight incubation at 37° C.

A sulfamethazine standard was prepared in methanol and then diluted in 0.1% BSA/PBS to provide solutions containing 1, 5 and 10 ppb. A negative control consisting of the diluent alone was also prepared. One hundred microliters of the standard solutions and the negative control were added to the immunoassay devices containing the samples of cellulose acetate and incubated for 1 minute at room temperature. One hundred microliters of a solution of horseradish peroxidase diluted to a final concentration of 1:10,000 in the enzyme diluent was added and allowed to incubate for 1 minute at room temperature. The membranes were then washed three times by adding approximately 1 ml of the wash solution. The enzyme substrate consisting of a solution of 7 drops of 3,3',5,5'-tetramethylbenzidine (TMB) and 7 drops of 0.02% $H_2O_2$ was added to each of the devices and allowed to incubate for 1 minute at room temperature. The results of each assay were immediately observed and recorded. The results are presented in Table I.

TABLE I

| Sample | Negative Control | 1 ppb | 5 ppb | 10 ppb | Comment |
|---|---|---|---|---|---|
| R13540 | Blue | White | White | White | Poor |
| R13541 | Blue | Blue | White | White | Better |
| R13542 | Blue | Blue | Faint Blue | White | Best |

In the immunoassay employing the R13542 sample of cellulose acetate which was the most dense of the samples, the assay performed according to design specification by correctly distinguishing between 5 ppb and 10 ppb levels of sulfamethazine without requiring an increased concentration of either the antibody or enzyme. In addition, the R13542 material provided a visual background against which the white positive result was more easily perceived.

Additional membranes comprised of R13542 and four more samples of cellulose acetate each of increasingly higher density were tested using the foregoing methods and standard solutions containing 2.5, 10 and 100 ppb of sulfamethazine. The results are presented in Table II.

TABLE II

| Sample | Negative Control | 2.5 ppb | 10 ppb | 100 ppb | Comment |
|---|---|---|---|---|---|
| R13542 | Blue | Lt. Blue | Gray-Blue | Gray-White | Poor |
| R13638 | Blue | Faint Blue | White | White | Good |
| R13639 | Blue | Lt. Blue | Blue-White | White | Best |
| R13640 | Blue | Lt. Blue | Gray-White | White | |
| R13641 | Blue | Lt. Blue | Blue-White | White | |

The results of this screening demonstrated that the R13639 material exhibited superior results by providing the most easily discerned reaction endpoints. The endpoints achieved using R13639 ranged from blue to white without a significant gray intermediate range.

The results of these screening tests indicate that cellulose acetate with a density of about 0.29 gm/cc performs optimally as a porous membrane according to the present invention.

EXAMPLE 2

Detection of Sulfamethazine in Raw Milk Using a Competitive Inhibition Assay

The feasibility of providing an assay that would detect 10 ppb sulfamethazine in undiluted raw milk using the rapid immunoassay device was tested by preparing raw milk samples spiked with 5, 10 and 20 ppb of sulfamethazine. Using the methodology of Example 1, spiked raw milk from two animals was tested to analyze the effect, if any, of milkfat on the flow rate of the device membrane and on non-specific binding. The results are presented in Table III.

TABLE III

| Spiked Sample | Negative Control | 5 ppb | 10 ppb | 20 ppb |
|---|---|---|---|---|
| Milk #1 | Blue | Lt. blue | White | White |
| Milk #2 | Blue | Lt. blue | White | White |

TABLE III-continued

| Spiked Sample | Negative Control | 5 ppb | 10 ppb | 20 ppb |
| --- | --- | --- | --- | --- |
| Diluent | Blue | Blue | White | White |

The results demonstrated that raw milk was a suitable sample for use with the rapid immunoassay device. Optimization of the results was achieved by adjusting the antibody and enzyme concentrations to produce a darker blue (negative) color at 5 ppb while maintaining a clear white (positive) color result at 10 ppb.

EXAMPLE 3

Determining the Optimal Antibody Concentration for the Detection of Sulfamethazine Using a Competitive Inhibition Assay In order to determine optimal antibody concentration for the detection of sulfamethazine, twenty-five microliter aliquots of an anti-sulfamethazine antibody diluted 1:300, 1:400 and 1:450 in 2% SPA/PBS buffer were bound to the porous membranes of rapid immunoassay devices according to the present invention. Samples spiked with sulfamethazine were analyzed according to the methodology of Example 1. The results are presented in Table IV.

TABLE IV

| Antibody | Negative Control | 1 ppb | 5 ppb | 10 ppb | Comments |
| --- | --- | --- | --- | --- | --- |
| 1:300 | Blue | Blue | Blue | White | slight background at 10 ppb |
| 1:400 | Blue | Lt. Blue | Lt. Blue | White | Sharp cut-off |
| 1:450 | Blue | Lt. Blue | White | White | false positive at 5 ppb |

The results indicated that by varying the antibody concentration, the sensitivity of the assay was adjusted to provide an accurate qualitative endpoint at a preselected concentration of analyte.

EXAMPLE 4

Determining the Optimal Enzyme Concentration for the Detection of Gentamicin Using a Competitive Inhibition Assay In order to determine the optimal concentration of HRP conjugated to gentamicin in an assay for the detection of gentamicin using a rapid immunoassay device according to the present invention, enzyme dilutions of 1:16,000, 1:18,000, 1:20,000 and 1:24,000 were tested according to the methodology of Example 1. Twenty-five microliters of an anti-gentamicin antibody diluted to a concentration of 1:8,000 in Antibody Diluent were added to each of the porous membranes employed in the assays. The results are presented in Table V.

TABLE V

| Enzyme | Negative Control | 5 ppb | 7.5 ppb | 10 ppb | 100 ppb |
| --- | --- | --- | --- | --- | --- |
| 1:16,000 | Blue | Lt Blue | Lt Blue | Gray/White | White |
| 1:18,000 | Blue | Lt Blue | Gray/Lt Blue | White | — |
| 1:20,000 | Blue | White | — | White | White |
| 1:24,000 | Blue | White | — | White | White |

The results indicated that by varying the concentration of the enzyme solution, the sensitivity of the assay was adjusted to provide an accurate qualitative endpoint at a preselected concentration of analyte.

EXAMPLE 5

Detection of Aflatoxin by a Competitive Inhibition Assay Using the Rapid Immunoassay Device Experiments were conducted to determine the optimal concentration of antibody for the detection of aflatoxin using a rapid immunoassay device according to the present invention. The experiments were conducted according to the methodology of Example 1. The enzyme solution was diluted to 1:20,000. The results are presented in Table VI.

TABLE VI

| Antibody | Control | 0.83 ppb | 1.67 ppb | 2.5 ppb | 3.33 ppb |
| --- | --- | --- | --- | --- | --- |
| 1:800 | Blue | Lt Blue | Lt Blue | White | White |
| 1:1,000 | Blue | White | White | — | White |
| 1:1,200 | Blue | Lt Blue | White | White | White |
| 1:2,000 | Blue | White | White | White | — |

The results indicated that a qualitative assay for the detection of varying amounts of aflatoxin using a rapid immunoassay device according to the present invention was provided by adjusting the concentration of the antibody directed against aflatoxin relative to its concentration.

EXAMPLE 6

Detection of Progesterone by a Competitive Inhibition Assay Using the Rapid Immunoassay Device Experiments to determine the feasibility of detecting the presence of 10 ppb of progesterone in a sample using a rapid immunoassay device according to the present invention were conducted. The experiments were conducted according to the methodology of Example 1. Progesterone standards were prepared by diluting progesterone in 0.1% BSA/PBS. The HRP enzyme was diluted to 1:24,000. Anti-progesterone antibody was diluted 1:500 in Antibody Diluent. The results are shown in Table VII.

TABLE VII

| Negative Control | 1 ppb | 10 ppb | 100 ppb |
| --- | --- | --- | --- |
| Blue | Blue | White | White |

The results demonstrated that it was feasible to provide an assay using the rapid immunoassay device which could be used to screen samples for progesterone in amounts greater than or equal to 10 ppb.

EXAMPLE 7

Detection of Anti-Pasteurella Antibody by a Sandwich Immunoassay Using the Rapid Immunoassay Device Experiments were performed in order to determine the feasibility of using a rapid immunoassay device according to the present invention in a sandwich immunoassay for the detection of circulating antibody. Twenty-five microliters of an inactivated bacterial suspension of *Pasteurella multocida*, available from Agrilabs, Ltd, diluted 1:100 in PBS was applied to the porous membranes of rapid immunoassay devices and dried overnight at 37° C. Fifty microliters of a rabbit serum sample was then added to the devices followed by 50 μl of anti-rabbit antibody conjugated to HRP diluted 1:1,000 in a diluent comprising 0.01M phosphate, pH 7.4, 0.15M NaCl, 1% bovine serum albumin, 0.5% trehalose with 0.01% thimerosal. The membranes were washed three times by adding approximately 1 ml of PBS-Tween. TMB substrate was then added according to the methodology of Example 1. The results are presented in Table VIII.

TABLE VIII

| Serum Sample | Color Development | Comment |
|---|---|---|
| Rabbit | 5/6 Blue | 5/6 Positive for antibody against *P. multocida* |
| Sheep | 3/3 White | 3/3 Negative |

The results indicated that it was conduct a sandwich immunoassay utilizing the rapid immunoassay device. The majority of rabbit serum samples tested positive for antibody to *P. multocida* as expected, while no color development was detected using the sheep serum samples which served as negative controls.

EXAMPLE 8

Detection of Human Chorionic Gonadotropin (HCG) by a Sandwich Immunoassay Using the Rapid Immunoassay Device Experiments were performed in order to determine the feasibility of using a rapid immunoassay device according to the present invention in a sandwich immunoassay for the detection of an antigen. Rabbit anti-HCG antibody was bound to the porous membranes of rapid immunoassay devices according to the methodology of Example 1. Twenty-five microliters of a solution of HCG (5000 IU) was added to 50 μl of mouse anti-HCG antibody conjugated to alkaline phosphatase and allowed to incubate for 1 minute at room temperature. All of this solution was then added to the device and incubated for 2 minutes at room temperature. The device was washed three times (3X) with carbonate buffer. One hundred microliters of the BCIP chromophore solution was added. Color development was recorded after 2 minutes of incubation at room temperature. The results are presented in Table IX.

TABLE IX

| Sample | Color Development | Comments |
|---|---|---|
| HCG Spiked | Gray/Blue | Positive |
| Buffer Control | White | Negative |

The results indicate that a sandwich immunoassay was effective in detecting HCG in the amount present in the spiked samples employed in the foregoing experiments using the rapid immunoassay device.

EXAMPLE 9

Detection of Gentamicin and Neomycin by a Cascade Assay Using the Rapid Immunoassay Device The rapid immunoassay device can be utilized in either sandwich or competitive cascade assays designed to indicate the presence of two analytes in a sample in concentrations as low as parts per trillion. Cascade assays utilize two enzyme substrate systems, wherein the product of the first enzyme/substrate reaction serves as the substrate in the second enzyme/substrate reaction. In order to detect the combination of gentamicin and neomycin in a sample, gentamicin would be labelled with horse radish peroxidase (HRP) using standard techniques and then diluted to concentrations appropriate for the assay in PBS/T. Neomycin would be labelled with glucose oxidase and then diluted in PBS/T. A sample solution containing appropriate concentrations of both analytes is then prepared by mixing the foregoing solutions. Anti-gentamicin and anti-neomycin antibodies are bound to the porous membrane member of a rapid immunoassay device according to the methodology of Example 1. One hundred microliter samples of PBS/T and samples containing gentamicin alone, neomycin alone, and gentamicin and neomycin in combination can then be tested for the presence of the combination of analytes. Except for the composition of the enzyme substrate solution, the methodology of Example 1 would be employed. To prepare the enzyme substrate, a solution of TMB is prepared as in Example 1, except that a solution of glucose replaces hydrogen peroxide. The reaction of glucose oxidase with TMB will produce hydrogen peroxide which then serves as the substrate for HRP. The expected results of the cascade assay are presented in Table X.

TABLE X

| Sample | Color Development |
|---|---|
| PBS/T | White |
| Neomycin | White |
| Gentamicin | White |
| Gentamicin & Neomycin | Blue |

What is claimed is:

1. An apparatus for use in immunoassay procedures consisting essentially of:
   (A) a housing comprising a reservoir member and a base member, said reservoir member defining a cavity, said base member engaging said reservoir member to enclose said cavity, and having
      (i) a first surface on said reservoir member facing away from said cavity and a second surface on said reservoir member facing into said cavity;
      (ii) an aperture providing an opening through both of said first and second surfaces,
      (iii) a first profile provided on said first surface around said aperture,
      (iv) at least one vent hole,
      (v) a second profile facing said cavity provided on said second surface around said aperture;
   (B) a single porous foam member provided in said cavity, wherein a surface of said foam member is deformable by said second profile to produce a depression that surrounds an area on said surface of said foam member; and
   (C) a reagent-binding member provided on said surface of said foam member within said area on said surface of said foam member wherein no external means to direct the flow of sample and reagents within said apparatus is required.

2. An apparatus according to claim 1, wherein said first profile is conical.

3. An apparatus according to claim 1, wherein said second profile has a circular cross section.

4. An apparatus according to claim 1, wherein said porous foam member is comprised of a material selected from the group consisting of fibers of cellulose or cellulose derivatives, glass, ceramic and non-cellulose hydrocarbon materials.

5. An apparatus according to claim 1, wherein said reagent-binding member is comprised of Staphylococcal protein A.

6. An apparatus according to claim 1, wherein said reagent-binding member is comprised of Staphylococcal protein G.

7. An apparatus according to claim 1, wherein said reagent-binding member is comprised of latex particles.

8. An apparatus according to claim 5, which further comprises antibodies which specifically bind an analyte selected from the group consisting of antibiotics, mycotoxins, drugs of abuse, hormones, and bacterial antigens, said antibodies being bound to said reagent-binding member.

9. An apparatus according to claim 8, wherein said analyte is a coccidiostat.

10. An apparatus according to claim 8, wherein said analyte is sulfamethazine, gentamicin, aflatoxin, zearalenone, monensin, tylosin, opiates, amphetamines, methamphetamines, cocaine, barbiturates, progesterone, human chorionic gonadotropin, or *Pasteurella multocida* antigen.

11. A kit for determining an analyte in a sample, comprising an apparatus according to claim 8 and, in a separate container, an antibody which specifically binds said analyte and which is conjugated to an enzyme.

12. A kit according to claim 11, wherein said enzyme is horseradish peroxidase, glucose oxidase, or alkaline phosphatase.

13. A kit for determining an analyte in a sample, comprising an apparatus according to claim 8, and, in a separate container, an analyte as recited in claim 8 conjugated to an enzyme.

14. A kit according to claim 13, wherein said enzyme is horseradish peroxidase, glucose oxidase, or alkaline phosphatase.

15. An apparatus according to claim 6, which further comprises antibodies which specifically bind an analyte selected from the group consisting of antibiotics, mycotoxins, drugs of abuse, hormones, and bacterial antigens, said antibodies being bound to said reagent-binder member.

16. An apparatus according to claim 15, wherein said analyte is a coccidiostat.

17. An apparatus according to claim 15, wherein said analyte is sulfamethazine, gentamicin, aflatoxin, zearalenone, monensin, tylosin, opiates, amphetamines, methamphetamines, cocaine, barbiturates, progesterone, human chorionic gonadotropin, or *Pasteurella multocida* antigen.

18. A kit for determining an analyte in a sample, comprising an apparatus according to claim 15 and, in a separate container, an antibody which specifically binds said analyte and which is conjugated to an enzyme.

19. A kit according to claim 18, wherein said enzyme is horseradish peroxidase, glucose oxidase, or alkaline phosphatase.

20. A kit for determining an analyte in a sample, comprising an apparatus according to claim 15, and, in a separate container, an analyte as recited in claim 15 conjugated to an enzyme.

21. A kit according to claim 20, wherein said enzyme is horseradish peroxidase, glucose oxidase, or alkaline phosphatase.

22. An apparatus according to claim 7, which further comprises antibodies which specifically bind an analyte selected from the group consisting of antibiotics, mycotoxins, drugs of abuse hormones, and bacterial antigens, said antibodies being bound to said reagent-binding member.

23. An apparatus according to claim 22, wherein said analyte is a coccidiostat.

24. An apparatus according to claim 22, wherein said analyte is sulfamethazine, gentamicin, aflatoxin, zearalenone, monensin, tylosin, opiates, amphetamines, methamphetamines, cocaine, barbiturates, progesterone, human chorionic gonadotropin, or *Pasteurella multocida* antigen.

25. A kit for determining an analyte in a sample, comprising an apparatus according to claim 22 and, in a separate container, an antibody which specifically binds said analyte and which is conjugated to an enzyme.

26. A kit according to claim 25, wherein said enzyme is horseradish peroxidase, glucose oxidase, or alkaline phosphatase.

27. A kit for determining an analyte in a sample, comprising an apparatus according to claim 22, and, in a separate container, an analyte as recited in claim 22 conjugated to an enzyme.

28. A kit according to claim 27, wherein said enzyme is horseradish peroxidase, glucose oxidase, or alkaline phosphatase.

* * * * *